US011274362B2

(12) United States Patent
Azar et al.

(10) Patent No.: US 11,274,362 B2
(45) Date of Patent: Mar. 15, 2022

(54) BIORESORBABLE MATERIALS, BIORESORBABLE MEDICAL DEVICES, BIORESORBABLE COATINGS FOR IMPLANTABLE MEDICAL DEVICES AND METHOD OF MANUFACTURING THE SAME USING VAPOR DEPOSITION

(71) Applicants: Toufic Azar, Montreal (CA); Renzo Cecere, Town of Mont Royal (CA); Norma Yadira Mendoza Gonzalez, Montreal (CA); Jean-Luc Meunier, Montreal (CA); Rosaire Mongrain, Montreal (CA)

(72) Inventors: Toufic Azar, Montreal (CA); Renzo Cecere, Town of Mont Royal (CA); Norma Yadira Mendoza Gonzalez, Montreal (CA); Jean-Luc Meunier, Montreal (CA); Rosaire Mongrain, Montreal (CA)

( * ) Notice: Subject to any disclaimer, the term of this patent is extended or adjusted under 35 U.S.C. 154(b) by 423 days.

(21) Appl. No.: 15/783,892

(22) Filed: Oct. 13, 2017

(65) Prior Publication Data

US 2018/0071121 A1 Mar. 15, 2018

Related U.S. Application Data

(63) Continuation-in-part of application No. 14/837,904, filed on Aug. 27, 2015, now abandoned.
(Continued)

(51) Int. Cl.
*C23C 14/32* (2006.01)
*C23C 14/14* (2006.01)
(Continued)

(52) U.S. Cl.
CPC .............. *C23C 14/325* (2013.01); *A61F 2/07* (2013.01); *A61F 2/91* (2013.01); *A61L 31/08* (2013.01);
(Continued)

(58) Field of Classification Search
CPC ....... C23C 14/14; C23C 14/325; C23C 14/00; C23C 14/22; C23C 14/24; C23C 14/243;
(Continued)

(56) References Cited

U.S. PATENT DOCUMENTS 5,103,766 A * 4/1992 Yoshikawa ....... H01J 37/32055
118/723 VE
6,027,619 A * 2/2000 Cathey .................. C23C 14/046
204/192.38
(Continued)

FOREIGN PATENT DOCUMENTS

CA  2674195    7/2008
CA  2727568    12/2009
(Continued)

OTHER PUBLICATIONS

Baddour, Carole Emilie. Direct growth of carbon nanotubes on metal surfaces without an external catalyst and nanocomposite production. Dec. 2010 PhD Thesis. Montréal: McGill University.

*Primary Examiner* — Michael A Band

(57) ABSTRACT

A method for manufacturing an implantable medical device, the method including the steps of: (a) providing in a vapor deposition chamber a substrate including a substrate material, an anodic source made of an anodic material, and a cathodic source made of a cathodic material, the anodic and cathodic materials forming a galvanic couple; (b) operating the vapor deposition chamber to vaporize simultaneously the anodic and cathodic materials from the anodic and cathodic sources and depositing the vaporized cathodic and anodic materials on the substrate to produce a coated substrate
(Continued)

including the substrate material coated by a bioresorbable coating; and (c) obtaining the implantable medical device from the coated substrate. Also, a stent, a medical device and a bioresorbable material obtained with vapor deposition of materials forming a galvanic couple.

18 Claims, 9 Drawing Sheets

Related U.S. Application Data

(60) Provisional application No. 62/043,872, filed on Aug. 29, 2014.

(51) Int. Cl.
| | |
|---|---|
| *C23C 14/16* | (2006.01) |
| *A61F 2/07* | (2013.01) |
| *A61F 2/91* | (2013.01) |
| *A61L 31/08* | (2006.01) |
| *A61L 31/16* | (2006.01) |
| *A61L 31/14* | (2006.01) |

(52) U.S. Cl.
CPC .............. *A61L 31/16* (2013.01); *C23C 14/14* (2013.01); *C23C 14/16* (2013.01); *A61F 2210/0004* (2013.01); *A61F 2240/001* (2013.01); *A61L 31/148* (2013.01); *A61L 2420/02* (2013.01)

(58) Field of Classification Search
CPC ......... C23C 14/26; C23C 14/28; C23C 14/30; C23C 14/32; A61F 2/915; A61F 2/91; A61F 2/07; A61F 2/86; A61F 2/82; A61F 2210/0004; A61L 31/16; A61L 31/148; A61L 31/08; A61L 2420/02
See application file for complete search history.

(56) References Cited

U.S. PATENT DOCUMENTS

| | | | |
|---|---|---|---|
| 6,602,390 B1 * | 8/2003 | Brandie | C23C 14/325 |
| | | | 118/723 VE |
| 6,645,354 B1 * | 11/2003 | Gorokhovsky | C23C 14/0605 |
| | | | 204/192.38 |
| 6,663,755 B2 * | 12/2003 | Gorokhovsky | C23C 14/022 |
| | | | 204/192.38 |
| 6,780,458 B2 | 8/2004 | Seth et al. | |
| 7,514,122 B2 | 4/2009 | Kramer | |
| 7,572,287 B2 | 8/2009 | Stinson | |
| 7,854,958 B2 | 12/2010 | Kramer | |
| 7,989,093 B2 * | 8/2011 | Myrtveit | C23C 14/0641 |
| | | | 204/192.1 |
| 8,002,821 B2 | 8/2011 | Stinson | |
| 8,080,055 B2 | 12/2011 | Atanasoska et al. | |
| 8,354,120 B2 * | 1/2013 | Weber | A61F 2/0077 |
| | | | 424/424 |
| 10,028,847 B2 * | 7/2018 | Mongrain | B22F 3/24 |
| 2004/0055538 A1 * | 3/2004 | Gorokhovsky | C23C 14/0641 |
| | | | 118/715 |
| 2006/0112536 A1 | 6/2006 | Herweck et al. | |
| 2007/0219626 A1 | 9/2007 | Rolando et al. | |
| 2008/0058919 A1 | 3/2008 | Kramer-Brown | |
| 2008/0294236 A1 * | 11/2008 | Anand | C23C 14/06 |
| | | | 623/1.15 |
| 2010/0069717 A1 * | 3/2010 | Hafezi | H01M 4/668 |
| | | | 600/117 |
| 2011/0060419 A1 | 3/2011 | Choi | |
| 2012/0101565 A1 | 4/2012 | Stinson | |
| 2015/0094798 A1 | 4/2015 | Mongrain et al. | |

FOREIGN PATENT DOCUMENTS

| | | | |
|---|---|---|---|
| EP | 1858564 | 11/2007 | |
| WO | WO-0155473 A1 * | 8/2001 | ......... C23C 14/0005 |
| WO | 2010/034098 | 4/2010 | |

* cited by examiner

BIORESORBABLE MATERIALS, BIORESORBABLE MEDICAL DEVICES, BIORESORBABLE COATINGS FOR IMPLANTABLE MEDICAL DEVICES AND METHOD OF MANUFACTURING THE SAME USING VAPOR DEPOSITION

FIELD OF THE INVENTION

The present invention relates to the art of medical devices. More specifically, the present invention is concerned with bioresorbable medical devices, such as stents for example, and a method of manufacturing the same using a vapor deposition process. The present invention also relates to bioresorbable materials and bioresorbable coatings for implantable medical devices.

BACKGROUND

Bioresorbable stents have been shown to be advantageous in the treatment of many medical conditions. Many stents take the form of a scaffold, with some having relatively small struts, for example struts of a few tens of microns. One method of promoting bioresorption in a stent is to manufacture the stent out of particles or grains of different materials that form a galvanic couple. However, such particles need to be relatively small due to the small size of the struts in many stents. Current method of manufacturing such stents result in particles of one or more microns, which may negatively affect the material properties of the stent as the grains are only slightly smaller than the structural elements of the stent. Other types of bioresorbable implantable medical devices and coatings for such devices also present the same inconvenients.

Accordingly, there is a need in the industry to provide an improved bioresorbable stent and other bioresorbable medical devices, along with methods of manufacturing such medical devices and materials having suitable bioresorption properties. An object of the present invention is therefore to provide such devices, methods and materials.

SUMMARY OF THE INVENTION

In a broad aspect, there is provided a method for manufacturing an implantable medical device, the method comprising the steps of: (a) providing in a vapor deposition chamber a substrate including a substrate material, an anodic source made of an anodic material, and a cathodic source made of a cathodic material, the anodic and cathodic materials forming a galvanic couple; (b) operating the vapor deposition chamber to vaporize simultaneously the anodic and cathodic materials from the anodic and cathodic sources and depositing the vaporized cathodic and anodic materials on the substrate to produce a coated substrate including the substrate material coated by a bioresorbable coating formed by deposition of the vaporized cathodic and anodic materials; and (c) obtaining the implantable medical device from the coated substrate. The anodic and cathodic materials are deposited in a predetermined ratio and are selected so that bioresorption of the bioresorbable of at least part of the implantable medical device stent is promoted by galvanic corrosion between the anodic and cathodic materials when the implantable medical device is implanted in vivo.

There may also be provided a method wherein the substrate material differs from both the anodic and cathodic materials.

There may also be provided a method wherein the substrate material is identical to one of the anodic and cathodic materials.

There may also be provided a method wherein the anodic and cathodic materials are metallic.

There may also be provided a method wherein the anodic material is selected from the group consisting of iron, iron alloys and vanadium and the cathodic material is selected from the group consisting of cobalt-chromium alloys, stainless steel, tantalum, titanium and platinum-steels.

There may also be provided a method wherein the anodic material and cathodic materials are selected from the group of couples consisting of iron/stainless steel and iron/tantalum.

There may also be provided a method wherein at least one of the anodic and cathodic materials is an alloy.

There may also be provided a method wherein at least one of the anodic and cathodic materials is stainless steel.

There may also be provided a method wherein the anodic material and cathodic materials are respectively iron and stainless steel.

There may also be provided a method wherein the anodic and cathodic materials are biocompatible.

There may also be provided a method wherein the predetermined ratio is from about 1:1 to about 4:1 w/w in the anodic material with respect to the cathodic material.

There may also be provided a method wherein the substrate material differs from the anodic and cathodic materials, and step (c) includes exposing at least part of the substrate material; and removing at least part of the substrate material from the coated substrate.

There may also be provided a method wherein removing at least part of the substrate material includes removing essentially all the substrate material so that the implantable medical device is made essentially of the deposited bioresorbable coating.

There may also be provided a method wherein the substrate material is soluble in a solvent, removing essentially all the substrate material including dissolving the substrate material in the solvent.

There may also be provided a method wherein step (c) further includes cutting out portions of the bioresorbable coating.

There may also be provided a method wherein the substrate is substantially cylindrical and defines two substantially opposed cylinder end surfaces, the method further comprising covering with a covering element at least one of the cylinder end surfaces before step (b) and wherein step (c) includes removing the covering element.

There may also be provided a method wherein in step (b), the relative proportions of the anodic and cathodic materials vaporized, parameters of the vapor deposition process or both the relative proportions of the anodic and cathodic materials vaporized and parameters of the vapor deposition process are varied in time during operation of the vapor deposition chamber to create a non-homogeneous composition in the bioresorbable coating.

There may also be provided a method wherein the implantable medical device is a stent, and wherein the substrate includes a plurality of struts, the substrate being substantially entirely covered with the anodic and cathodic materials in step (b).

There may also be provided a method wherein the vapor deposition chamber is selected from vapor deposition chambers operable to perform a vapor deposition process selected from a physical vapor deposition (PVD) cathodic arc deposition (arc-PVD), electron beam physical vapor deposition, evaporative deposition, pulsed laser deposition, sputter deposition, magnetron sputtering, a chemical vapor deposition (CVD), aerosol assisted CVD (AACVD), direct liquid injection CVD (DLICVD), a plasma vapor deposition, microwave plasma-assisted CVD (MPCVD), plasma-enhanced CVD (PECVD), remote plasma-enhanced CVD (RPECVD), atomic-layer CVD (ALCVD), combustion chemical vapor deposition (CCVD), hot filament CVD (HFCVD), hybrid physical-chemical vapor deposition (HPCVD), metalorganic chemical vapor deposition, rapid thermal CVD (RTCVD), vapor-phase epitaxy (VPE) and photo-initiated CVD (PICVD).

There may also be provided a method wherein in step (b), the vapor deposition chamber is operated under conditions resulting in deposition of the bioresorbable material with grains, at least 99% of the grains being smaller than 100 nm.

There may also be provided a method wherein in step (b), the vapor deposition chamber is operated under conditions resulting in deposition of the bioresorbable material with grains, at least 98.5% of the grains being smaller than 100 nm.

There may also be provided a method wherein in step (b), the vapor deposition chamber is operated under conditions resulting in deposition of the bioresorbable material with grains, at least 95% of the grains being smaller than 100 nm.

There may also be provided a method wherein at least 99% of the grains are smaller than 10 nm.

There may also be provided a method wherein at least 98.5% of the grains are smaller than 10 nm.

There may also be provided a method wherein at least 95% of the grains are smaller than 10 nm.

There may also be provided a method wherein in step (b), the vapor deposition chamber is operated under conditions resulting in deposition of the bioresorbable material in the form of a continuous material including grains smaller than 100 nm.

There may also be provided a method wherein particles larger than 100 nm are dispersed in the continuous material.

There may also be provided a method wherein the vapor deposition chamber is a cathodic arc physical vapor deposition chamber.

There may also be provided a method wherein the substrate is biased at a negative voltage.

There may also be provided a method wherein the negative voltage is between −10V and −1000V.

There may also be provided a method wherein the negative voltage is about −150V.

There may also be provided a method wherein step (b) includes rotating the substrate while operating the vapor deposition chamber.

There may also be provided a method wherein the substrate includes a metal coated with a carbon nanotube forest, the carbon nanotubes being exposed to the vaporized cathodic and anodic materials in step (b).

There may also be provided a method wherein the implantable medical device is selected from the group consisting of a markers, anchors, clips, sutures, orthopaedic support devices, artificial cardiac pumps and stents.

The term "bioresorbable material" designates the material obtained by deposition of the vaporized anodic and cathodic materials.

Advantageously, vapor deposition manufactured devices and coatings have relatively good structural strength since the particle size can reach the nanometer scale. In addition, the process results in a relatively homogeneous material when performed with suitable parameters. The smaller particle size leads to an increase in the area of corrosion, leading to potentially a faster bioresorbability rate with better diffusion of saline solution and better control of that rate when compared with materials having larger particles. The adhesion process is either mechanical or chemical.

In embodiments in which mechanical adhesion is used, cathodic arc deposition can be used. This physical vapor deposition method has several advantages: due to high level of atom ionization in a plasma, which is caused by having a very energetic process, materials (for example elements, such as metals) used in the manufacturing process can be co-evaporated at the same rate, thus producing stoichiometric compounds. Also, better adhesion between the various materials can be achieved as a result of the intermixed reaction zone. Furthermore, relatively low processing temperatures allow for the coating of heat-sensitive substrates/components. Yet furthermore, by changing the materials used as the manufacturing process proceeds, or the relative evaporation rates between different source materials placed in the same coating chamber, either multilayered coatings and functionally graded compositions or mixed structure coatings with very local functionalities can easily be produced. In addition because the process does not require direct line of sight, in contrast to other methods such as cold-spray or hot-spray, complex geometries can be coated or created with physical vapor deposition.

More specifically, the present patent application proposes a new application of vapor deposition, and particularly physical vapor deposition to form a material with controllable biodegradability as a coating or as the whole body of a medical device, or any other type of device. While most coating in medical devices are there to prevent corrosion on a surface of a device, the present invention intends to do the opposite and promote the corrosion of the surface or the whole device formed by mixing two or more galvanic metals one acting as a cathode the other as the anode. In addition, it is within the scope of the invention to mix two cathodic materials and one anodic material, or intertwine other materials. The Intermix ratio, particle size, residual stress and oxidation level can be tailored by controlling the deposition rate, temperature, pressure, bias, current, gas composition and gas flow rate, among other parameters.

In some embodiments, the cathodic and anodic particles are substantially homogeneously dispersed in the bioresorbable material. In some embodiments, the implantable medical devices such as a stent, among other possibilities, is entirely made of the bioresorbable material. In other embodiments, the bioresorbable stent further comprises a non-bioresorbable portion. For example, and non-limitingly, the bioresorbable material is deposited on a polymer scaffold. In another non-limiting example, the scaffold includes a "forest" or a "felt" of carbon nanotubes, the bioresorbable material being attached to and surrounding each carbon nanotube producing an open architecture.

In yet another broad aspect, the invention provides a vapor deposited bioresorbable material obtained as described above.

In yet another broad aspect, the invention provides a method for manufacturing a bioresorbable device using the same steps described above with respect to the method for manufacturing a stent.

Advantageously, in some embodiments of the invention, a relatively small bioresorbable stent that is nevertheless strong and ductile enough can be manufactured using the proposed material.

In another broad aspect, the invention provides a stent, the stent including a bioresorbable material, the bioresorbable material being a vapor deposited material including cathodic grains and anodic grains bound to each other, wherein the anodic grains are made of an anodic material and the cathodic grains are made of a cathodic material, the anodic and cathodic materials forming a galvanic couple; the anodic and cathodic grains are present in a predetermined ratio in the bioresorbable material.

The invention may also provide a stent, or other implantable medical device, essentially made of the bioresorbable material.

The invention may also provide a stent wherein the stent, or implantable medical device, is entirely made of the bioresorbable material.

The invention may also provide a stent wherein the bioresorbable material is substantially non-porous. For example, this is achieved by having a material that has a porosity of about 0.2% or less, but other values of porosity are within the scope of the invention.

The invention may also provide a stent wherein the stent includes a frame of a frame material different from the bioresorbable material coated by the bioresorbable material. Such frame materials may be metallic or polymeric, for example.

The present application claims priority from U.S. patent application Ser. No. 14/837,904 filed Aug. 27, 2015, the contents of which is hereby incorporated by reference in its entirety.

Other objects, advantages and features of the present invention will become more apparent upon reading of the following non-restrictive description of preferred embodiments thereof, given by way of example only and in relation with the following Figures.

DETAILED DESCRIPTION

Figure 1:
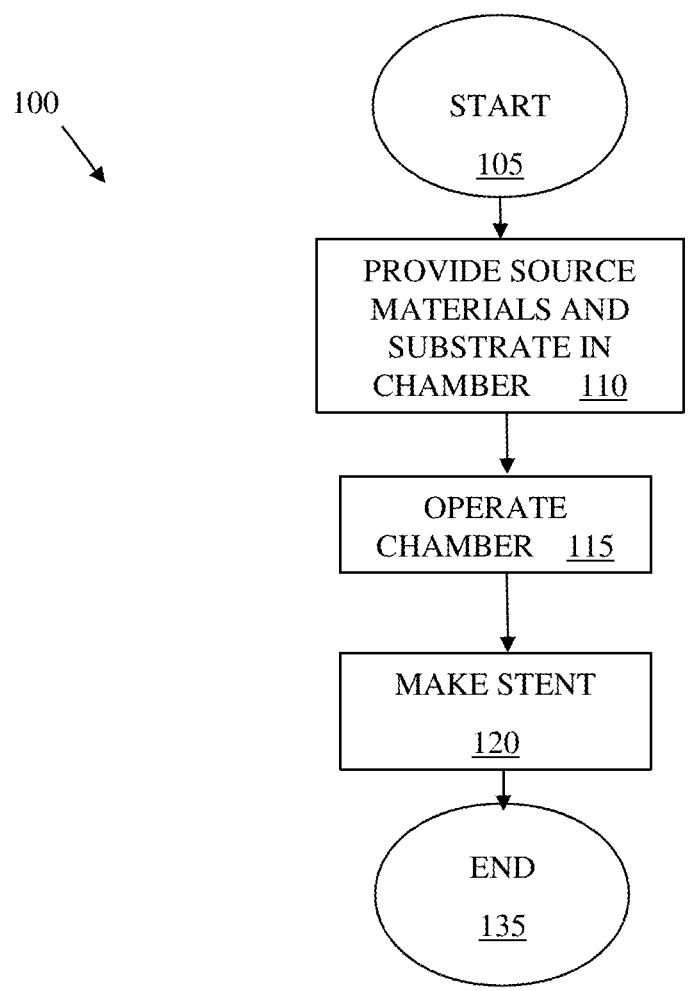
FIG. 1, in a flow chart, illustrates a method for manufacturing a implantable medical device in the form of a stent in accordance with an embodiment of the present invention.

The present invention relates to a novel material and to completely or partially bioresorbable implantable medical devices including this material. Also, as detailed hereinbelow, methods of manufacturing the material and medical devices are provided. While the following description mostly refers to a stent manufactured using the proposed material, it is within the scope of the invention to manufacture any suitable medical device using this material, such as, for example, orthopaedic devices used as temporary support while tissues heal, or implants, such as joint replacement implants, that are coated with the proposed material. Also, while the proposed material is well suited to the manufacture of bioresorbable medical devices, any other medical devices can be manufactured using the proposed material. Finally, while a specific method of manufacturing the proposed medical devices is proposed, in an alternative embodiment of the invention, the medical devices are manufactured using any other suitable method.

Vapor deposition processes are processes during which one or more sources of materials, also called targets in some processes, are vaporized in a chamber. The vaporized material is deposited on a substrate, and other surfaces in the chamber. Preferential deposition on the substrate can be promoted by applying a suitable potential difference between the substrate and other parts of the chamber. When sources having different compositions are used, a substrate can be coated in a material that is a mixture of the various substances included in the sources.

The present application describes a material manufactured through a vapor deposition process and some of its applications. The material has an extremely surprising property in that using two sources of different compositions, for example metallic compositions, did not result in a material having a homogeneous composition, as would be expected by someone skilled in the art of vapor deposition. Instead, the proposed materials includes grains of different compositions, instead of grains of a same composition in the form of a mixture of the two compositions forming the sources.

Even more surprisingly, when two sources are made of similar metals or alloys forming a galvanic couple, for example iron and stainless steel, the resulting vapor deposited material shows galvanic corrosion properties compatible with a structure in which grains of different compositions forming galvanic couples are present in the same material. This is unexpected as one would assume that after vaporization, iron and stainless steel, which includes iron and other metals, would be deposited as an alloy of uniform composition. Such an alloy would not show the observed corrosion properties, as described in further details below.

The proposed material is a nanostructured bioresorbable materials usable in medical applications and manufactured using plasma based deposition techniques. The proposed material can be used by itself, without any other materials, to manufacture the implantable medical devices, or can be used to coat implantable medical devices including other materials. An implantable medical device is any device, with or without moving parts, that is intended to be implanted in a human or animal and left in the human or animal for an extended amount of time, for example at least many weeks, or permanently.

An exemplary method 100 for manufacturing an implantable medical device in accordance with the present invention is shown in FIG. 1. The method 100 is presented more specifically in the context of the manufacture of a bioresorbable stent 218 (seen for example in FIG. 3E), but the general steps presented hereinbelow can be adapted to manufacture any suitable medical device. The method starts at step 105. Then at step 110, anodic and cathodic sources 202 and 204 are provided, along with a substrate 206, in a vapor deposition chamber 200, all seen in FIG. 2 and further described hereinbelow. At step 115, the vapor deposition chamber 200 is operated to vaporize jointly and simultaneously the anodic and cathodic materials from the anodic and cathodic sources 202 and 204 and deposit the vaporized cathodic and anodic materials on the substrate 206 to produce a coated substrate 214 (seen for example in FIG. 3B) including the substrate material coated by a bioresorbable coating 216. Finally, the coated substrate 214 is processed to obtain the bioresorbable stent 218, or any other suitable bioresorbable implantable medical device, at step 120 and the method ends at step 125. The anodic and cathodic materials are deposited in a predetermined ratio and are selected so that bioresorption of the bioresorbable stent 218 is promoted by galvanic corrosion between the anodic and cathodic materials when the bioresorbable stent 218 is implanted in vivo.

It should be noted that step 120 may include many processes performed one after the other or may be as simple as obtaining the bioresorbable stent, or implantable medical device, 218 by removing the bioresorbable stent 218 from the vapor deposition chamber 200. Even in this last case, there is a need typically to separate the coated substrate 214 from its support in the vapor deposition chamber 200 as the vapor deposition process typically coats anything that is in the vapor deposition chamber 200 with a continuous layer.

For the purpose of this document, the term "the bioresorbable material" and "the bioresorbable coating" refer to a material and a coating respectively manufactured through vapor deposition as described above with deposition of the anodic and cathodic materials simultaneously and jointly.

Similar methods are used to manufacture other devices, for example other biomedical devices, such as markers, anchors, clips, sutures and orthopaedic support devices, among others.

Figure 2:
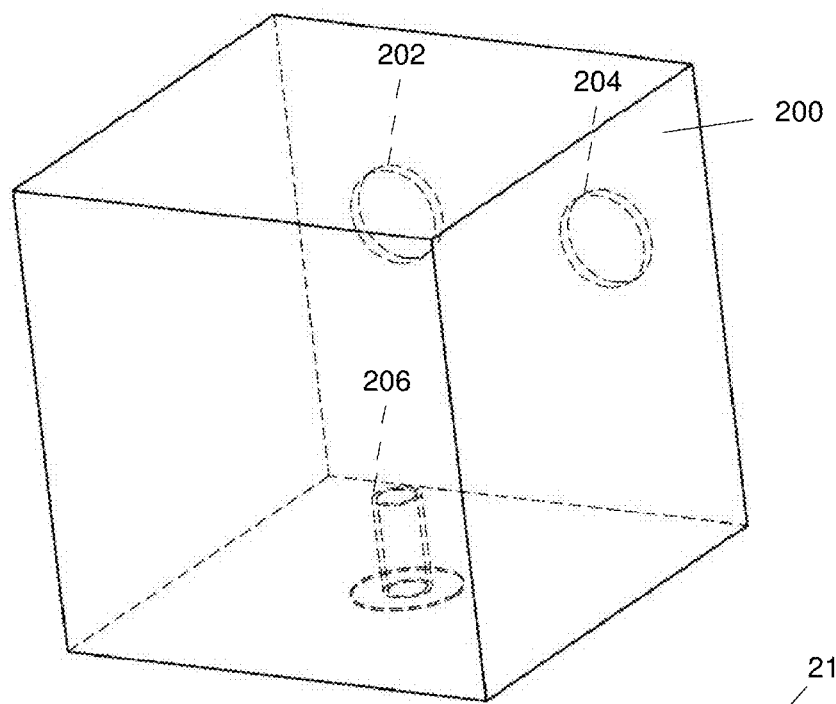
FIG. 2, in a schematic view, illustrates a setup usable to perform some steps of the method of FIG. 1.

Referring to FIG. 2, there is shown in schematic form a non-limiting example of a vapor deposition chamber 200 usable to perform the method 100. The vapor deposition chamber 200 is an enclosure that can be hermetically sealed and in which are provided a substrate 206 made of a substrate material, an anodic source 202 made of an anodic material, and a cathodic source 204 made of a cathodic material. The anodic and cathodic materials form a galvanic couple. The anodic material is electropositive relative to the cathodic material, which is therefore electronegative.

For example, the anodic and cathodic materials are metallic. In some embodiments, but not necessarily, the anodic and cathodic materials may be biocompatible. Examples of suitable anodic and cathodic materials include anodic materials selected from the group consisting of iron, iron alloys and vanadium and the cathodic materials selected from the group consisting of cobalt-chromium alloys, stainless steel, tantalum, titanium and platinum-steels. In specific embodiment of the invention, the anodic material and cathodic materials are selected from the group of couples consisting of iron/stainless steel and iron/tantalum. In some embodiments of the invention, at least one of the anodic and cathodic materials is an alloy. For example, at least one of the anodic and cathodic materials is stainless steel, and in a more specific example, the anodic material and cathodic materials are respectively iron and stainless steel. Other suitable anodic and cathodic materials are however usable in other embodiments of the invention.

In the case in which a bioresorbable stent 218 is manufactured, the bioresorbable stent 218 includes the bioresorbable material formed through vapor deposition in the method 100. The bioresorbable stent 218 may be entirely made of this bioresorbable material, or the bioresorbable stent 218' may also include other materials, such as some of the substrate material. This last case is illustrated in the sequence of FIGS. 4A and 4B, while the first case is illustrated in the sequence of FIGS. 3A to 3E.

More specifically, FIGS. 3A to 3E illustrate sequential steps in a method in which at least a portion of the substrate 206 is removed after vapor deposition. Typically, in these embodiments, the substrate material differs from the anodic and cathodic materials. In some embodiments, essentially all or all of the substrate 206 is removed. The term "essentially" denotes that some contamination may remain, such contamination being insufficient to render the stent 218 unsuitable for its intended purpose. To allow such removal, at least part of the substrate 206 must be exposed prior to removal. FIGS. 3A to 3E illustrate an example of such a method, but other methods are within the scope of the invention, for example such a method includes simply coating all the substrate 206 and then removing a thin slice of the coated substrate 214 prior to substrate 206 removal.

Figure 3A:
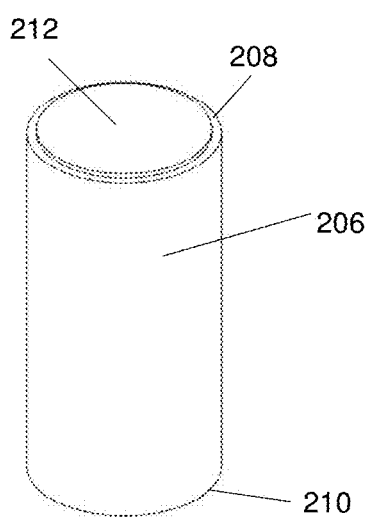
FIGS. 3A to 3E, in schematic views, illustrate successive steps in the manufacture of a stent using an embodiment of the method of FIG. 1.
Figure 4A:
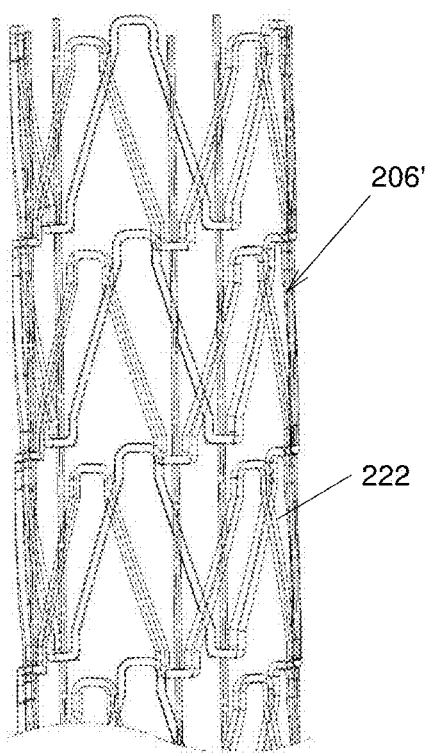
FIGS. 4A and 4B, in schematic views, illustrate successive steps in the manufacture of a stent using an other embodiment of the method of FIG. 1.
Figure 4B:
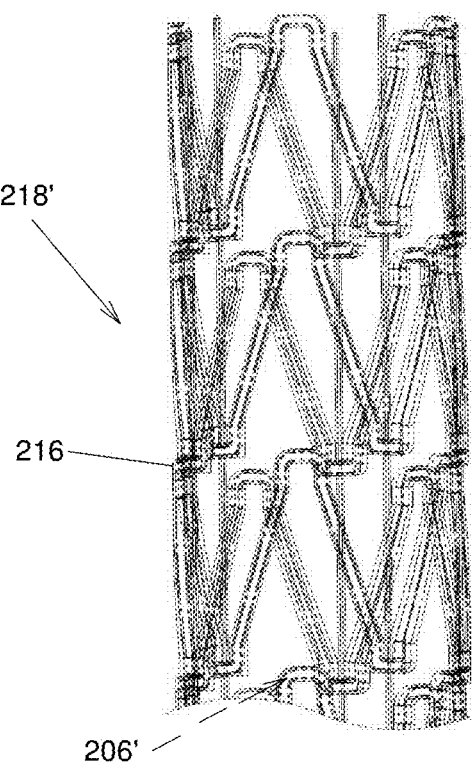

Referring to FIG. 3A, there is shown the substrate 206. In some embodiments, the substrate 206 is substantially cylindrical and defines two substantially opposed cylinder end surfaces 208 and 210. A cylindrical substrate 206 is convenient for manufacturing stents, for example. However, in alternative embodiments, the substrate 206 has any other suitable shape. In FIG. 3A, at least one of the cylinder end surfaces 208 and 210 has been covered with a covering element 212. For example, the cylinder end surface 210 is used to support the substrate 206 in the vapor deposition chamber 200, and therefore does not need covering. The other cylinder end surface 208 is covered with a covering element 212 prior to operation of the vapor deposition chamber 200. For example, and non-limitingly, the covering element 212 may be a piece of aluminum foil.

Figure 3B:
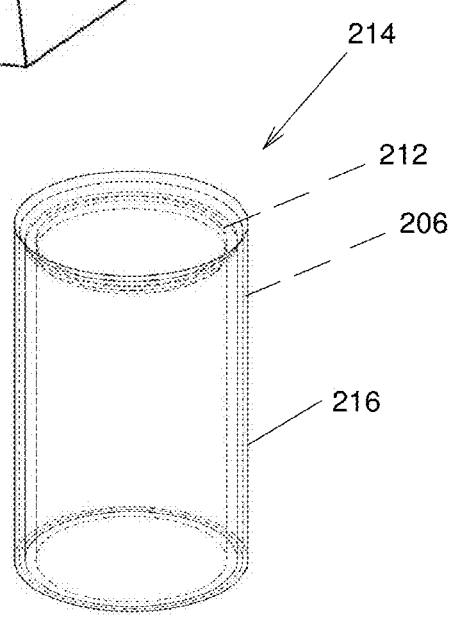

FIG. 3B illustrates the coated substrate 214, or in other words the substrate 206 covered by the bioresorbable coating 216. This configuration is achieved after step 115 shown in FIG. 1. Operation of the vapor deposition chamber 200 is performed under conditions required to achieve a suitable bioresorbable coating 216. For example the vapor deposition chamber 200 is selected from vapor deposition chambers operable to perform a vapor deposition process selected from a vapor deposition process selected from a physical vapor deposition (PVD) cathodic arc deposition (arc-PVD), electron beam physical vapor deposition, evaporative deposition, pulsed laser deposition, sputter deposition, magnetron sputtering, a chemical vapor deposition (CVD), aerosol assisted CVD (AACVD), direct liquid injection CVD (DLICVD), a plasma vapor deposition, microwave plasma-assisted CVD (MPCVD), plasma-enhanced CVD (PECVD), remote plasma-enhanced CVD (RPECVD), atomic-layer CVD (AACVD), combustion chemical vapor deposition (CCVD), hot filament CVD (HFCVD), hybrid physical-chemical vapor deposition (HPCVD), metalorganic chemical vapor deposition, rapid thermal CVD (RTCVD), vapor-phase epitaxy (VPE) and photo-initiated CVD (PICVD), among others.

The properties of the bioresorbable coating 216 depend on the specific vapor deposition process used and on the parameters of this vapor deposition process. Grain size is an important material property. In some embodiments, the vapor deposition chamber 200 is operated under conditions resulting in deposition of the bioresorbable material with grains, at least 99% of the grain in number being smaller than 100 nm. In yet other embodiments, at least 99% of the grains are smaller than 10 nm. In some embodiments, the vapor deposition chamber is operated under conditions resulting in deposition of the bioresorbable material in the form of a continuous material including grains smaller than 100 nm. Grains larger than 100 nm may be deposited, but such grains are dispersed in the continuous material. In other words, the bioresorbable material consists in a material in which a continuum of relatively small grains is contaminated by some larger grains. However, such larger grains are in relatively small numbers so that the bioresorbable material still has suitable mechanical properties.

In some embodiments, the relative proportions of the anodic and cathodic materials vaporized may be constant in time during the whole vapor deposition process. However, in other embodiments, the relative proportions of the anodic and cathodic materials vaporized is varied in time during operation of the vapor deposition chamber to create a non-homogeneous composition in the bioresorbable coating. This non-homogeneous composition creates a layered structure, with layers with either discrete changes in composition, or with layers that have continuously varied changes in composition between them. Since composition influences resorption rate, this layered structure can produce stents that are for example slowly resorbed initially, and then rapidly resorbed later, once the biological structure to support had time to heal and become less collapsible.

Since the substrate 206 is later removed in the sequence of FIGS. 3A to 3E, the thickness of the bioresorbable coating 216 is in some embodiments the thickness of the bioresorbable stent 218 that will be manufactured, for example between 5 μm and 200 μm.

Figure 3C:
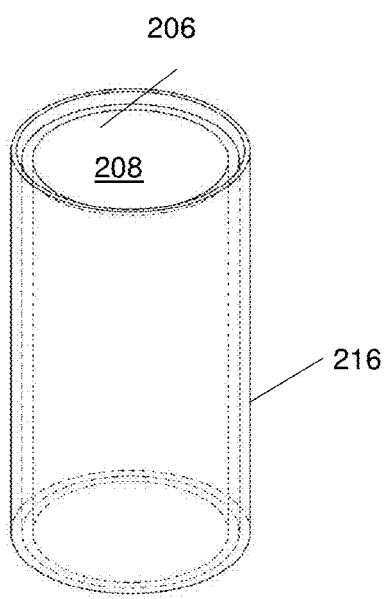

FIG. 3C illustrates the substrate 206 and bioresorbable coating 216 after the covering element 212 has been removed, therefore exposing the substrate 206, and more specifically the cylinder end surface 208. The covering element 212 can be removed for example by simply pulling thereonto if the bioresorbable coating 216 is sufficiently thin, fragile or brittle. In other embodiments, the bioresorbable coating 216 is cut adjacent the covering element 212, for example using a laser, which allows removal of the covering element. In yet other embodiments, a slice of the coated substrate 214 is removed adjacent the covering element 212.

In some embodiments, the substrate 206 is made of a material that can be removed relatively easily without damaging the bioresorbable coating 216. Typically, the substrate material differs from both the anodic and cathodic materials. For example, the substrate 206 has a relatively low melting temperature, lower than the melting temperature of the anodic and cathodic materials, and is removed by heating the coated substrate 214. In another example, the substrate 206 is soluble in a solvent in which the bioresorbable coating 216 is insoluble or only slightly soluble. When the bioresorbable coating 216 is made of a metal, a water-soluble substrate 206 may be used, such as substrate 206 made of a water-soluble ceramic, for example the ceramic commercialized under the name Aquacore™ by Advanced Ceramics Manufacturing. In some embodiments, the substrate 206 may be coated with a carbon nanotube forest, as described in "Baddour, Carole. Direct growth of carbon nanotubes on metal surfaces without an external catalyst and nanocomposite production. PhD Thesis. Montréal: McGill University, 2011", the contents of which is hereby incorporated by reference in its entirety. In such embodiments, the carbon nanotubes may facilitate formation of a suitable nanometer scale structure in the bioresorbable material as the vaporized anodic and cathodic materials are deposited thereonto.

Figure 3D:
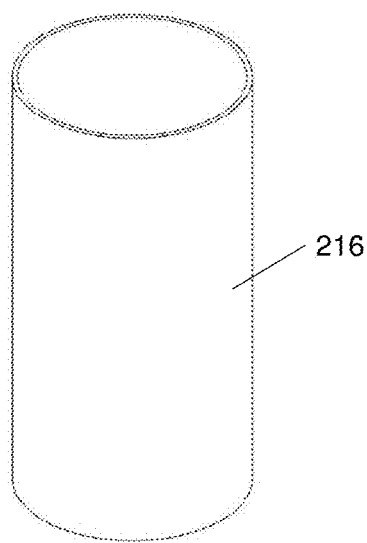
Figure 3E:
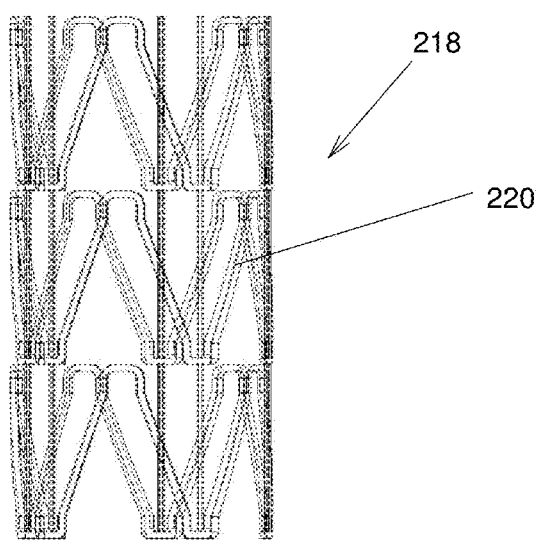

In some embodiments, essentially all the substrate material is removed. Traces of the substrate material may remain as contamination if such contamination is relatively small and does not render the bioresorbable stent 218 unsuitable for its purpose. After removal of the substrate 206, a hollow shell remains, as seen in FIG. 3D, after which a bioresorbable stent 218, seen in FIG. 3E, can be manufactured from this shell, for example by cutting out portions of the bioresorbable coating 216 to form struts 220, among other possibilities. Such cutting may be advantageously performed in some embodiment through laser cutting. Other processing of the bioresorbable stent 218 can be performed in step 120, such as coating with other materials, annealing, and cutting to specific dimensions, among others.

FIGS. 4A and 4B illustrate an alternative manner of performing the method 100. As seen in FIG. 4A, in this manner, the substrate 206' includes a plurality of struts 222. The struts 222 will be covered during the vapor deposition process, and as such can be relatively thin, for example about 5 to 10 μm thick. However, other thicknesses are within the scope of the invention. In a non-limiting example, the struts 222 are polymer struts. The coating 216 then improves the mechanical properties of the stent 218'. FIG. 4B illustrates the bioresorbable stent 218' after step 115 has been performed, as described hereinabove, with the bioresorbable coating 216 coating the substrate 206'. In this embodiment, the bioresorbable stent 218' includes a frame, in other words the substrate 206', which may differ from the bioresorbable material coated by the bioresorbable material. However, the substrate 206' is substantially entirely covered with the anodic and cathodic materials in step 115, and therefore can be one of the anodic and cathodic materials, or differ therefrom. Typically, a small portion of the substrate 206' used for supporting the substrate 206' during operation of the vapor deposition chamber 200 is left exposed. This portion can be covered through further deposition of left as is. For example, the bioresorbable coating 216 is made by vaporizing iron and stainless steel, and the substrate 206' is made of either iron or stainless steel. Another advantage provided by the bioresorbable coating 216 is that in some embodiments, the bioresorbable coating 216 provides a relatively smooth surface compared to some prior art stents.

While vapor deposition of two different materials has been described above, similar processes including vapor deposition of more than two materials are within the scope of the invention.

Example

Cathodic arc deposition or Arc-PVD is a physical vapor deposition technique in which an electric arc is used at low pressure to vaporize and ionize material from a cathode source material acting as the negative electrode. The ionized material forms high energy ions filling the coating chamber and condensing on a substrate, forming a thin film. The technique can be used to deposit metallic, ceramic, and composite films. It should be noted that the terms "cathode source" and "cathodic arc" deposition as used here relate to the manufacturing process and the plasma environment convention. This is not to be confused with the electrochemical labeling of the cathodic and anodic materials that form the claimed devices, stents and materials. Both the anodic and cathodic materials used in the device are vaporized from a cathode source, which here relates to the electrical potential at which the target is maintained during the manufacturing process. The anodic and cathodic materials may be provided in distinct targets used simultaneously or mixed together in a single target in which they are mixed in a predetermined ratio.

Some advantages of cathodic arc system are the control of the deposition environment from ion-beam based bombardment producing dense coatings to particle-based in situ nucleation with controlled particle size that can reach the nanometer scale. The particle size in the particle-based coatings generates a control over the resulting grain size, and a strongly reduced porosity in comparison to methods generating a coating from externally injected particles. Such systems also eliminate the need for line of sight coating geometry as the whole chamber is filled with plasma with particle nucleation occurring on the substrate, while re-sputtering effects also enable reaching around fine and complex shapes and allow to coat several complex geometries simultaneously. Moreover in the particle-based coating mode, the particles are either nucleating on the substrate or within the plasma environment close to the substrate from atomic and ionic precursors, and hence do not have high kinetic energies which allows for soft substrates, such as water soluble ceramics.

An industrial arc-based PVD deposition system (IonBond PVD 350) was used for the building of an iron (Fe)-stainless steel (SS) intermixed particulate material. Within this plasma based PVD technique, two metallic targets: Fe and SS are used to be vaporized in controlled vacuum and bias conditions. The resulting metallic vapor deposits into a substrate as nanoparticle composite. For the present work, two different substrates were used to deposit the Fe-SS material: ceramic and brass metal.

The deposition protocol used a continuous current arc discharge of 50 A on each of the metallic targets (for this work: Target 1: Fe, Target 2: SS) under a base vacuum of $1 \times 10^{-5}$ Torr or less and bias conditions for the carousel containing the samples to be coated of $-150$ V and deposition pressure of typically $1.2 \times 10^{-2}$ Torr Argon. As mentioned, the plasma ion beam composed of Ar, Fe and SS precursors is created with a continuous current arc discharge of 50 A with 80 sccm of argon injected as background gas. Deposition times from Fe and Stainless-Steel (SS) sources in low pressure argon were from some minutes to one hour. During all steps, the planetary carousel inside the chamber is rotated at 2 rpm to ensure that all the substrate surfaces pass through the plasma zones, resulting in uniform coating thickness. This process allowed tuning the arc-PVD parameters (specific vacuum chamber pressures, substrate temperature and bias, source currents).

All the mentioned arc-PVD parameters could be changed, thereby having a direct effect on the final deposited material. The following non-limiting exemplary parameter ranges could be used. Evaporator current is 50 A but it could be used from 30 to 100 A. The applied current should be high enough to sustain the arc spot that will ablate the metallic source. The carousel bias is set to $-150$V, but it can vary from 0 to $-1000$ V, a larger bias resulting in stronger attraction of the metallic vapor towards the substrate. The rotating speed of the carousel is set to 2 rpm but it can be varied from 1 to 3 rpm, for example and non-limitingly, as well as change rotation direction. The speed influences the time that the substrate passes through the plasma plume of each evaporator. Argon flow rate is typically 80 sccm for the presented cases but can be varied from 0 to 150 sccm, among other possibilities. This parameter increases the chamber pressure and therefore the particle size of the deposited material. Increasing the number of metallic targets has an influence on the deposition rate, leading to higher built of particles on the substrate.

Surface Characterization and Degradation Tests

The surface material characterization included: optical microscope, Scanning Electron Microscopy (SEM) and Transmission Electron Microscopy (TEM) with their corresponding chemical composition mapping (EDS). The chemical composition of bare ceramic and SS-Fe coating was analyzed by X-Ray Photoelectron Spectroscopy (XPS). Finally, Inductive Coupled Plasma (ICP) analysis was conducted to detect the amount of released chemical elements from the coated samples by monitoring 1 to 9 days of immersion in saline solution.

For the degradation tests two techniques were conducted. First, visual observation from immersion tests in saline solution, monitoring 1 to 5 days, was performed. Also, an electrochemical technique was performed. To that effect, immersion experiments were performed in Hank's solution with an initial pH of 7.4 and a temperature of 37° C. for a time period of 1 h. The corrosion behavior of plasma-prepared Fe-SS (ratio of 1:1), Fe, SS and non-treated SS (control) samples was investigated by open circuit potential (OCP), potentiodynamic polarization (PP) and electrochemical impedance spectroscopy (EIS) using a potentiostat/galvanostat (Autolab PGSTAT30). PP measurements were performed in the potential range from $-300$ mV to 400 mV with respect to OCP at a scan rate of 1 mV/s. EIS measurements were performed at OCP potential with AC amplitude of 10 mV over a frequency range from 10 mHz to 100 kHz. All measurements were done by duplicates.

Results

PVD coating tests have been carried on metallic and ceramic substrates. The metallic ones were used with the intention to use them for the degradation tests using immersion and electrochemical techniques. The ceramic substrates were used to simulate a soluble ceramic that could be removed after the coating process. Four different material combinations were deposited on the substrates: 1) Fe, 2) SS, 3) Fe-SS ratio 1:1 and 3) Fe-SS ratio 4:1. An average of 200 nm coating thickness was measured with a Dektak profilometer after 25 minutes processing.

The samples were observed through an optical and Scanning Electron Microscopy (SEM) microscope and showed the presence of a homogeneous and uniform structure. Observation of the SEM images showed that both Fe-SS ratios resulted in the presence of mostly nano scale particles, and very few micron sized particles. Transmission Electron microscopy confirmed the presence of nano particles from 2 to 50 nm in size. EDX analysis confirmed that Fe is the main constituent of the deposited material.

Immersion tests of 5 days in saline solution show the possibility to control the degradation rate. Visual inspection of the samples with a ratio of 4:1 presented more degradation than the samples with a ratio of 1:1. Weight measurements show the loss of material after the immersion test: Case 1 (Fe-SS ratio 1:1): 1.1 milligram Case 2 (Fe-SS ratio 4:1): 2 milligram.

Figure 5:
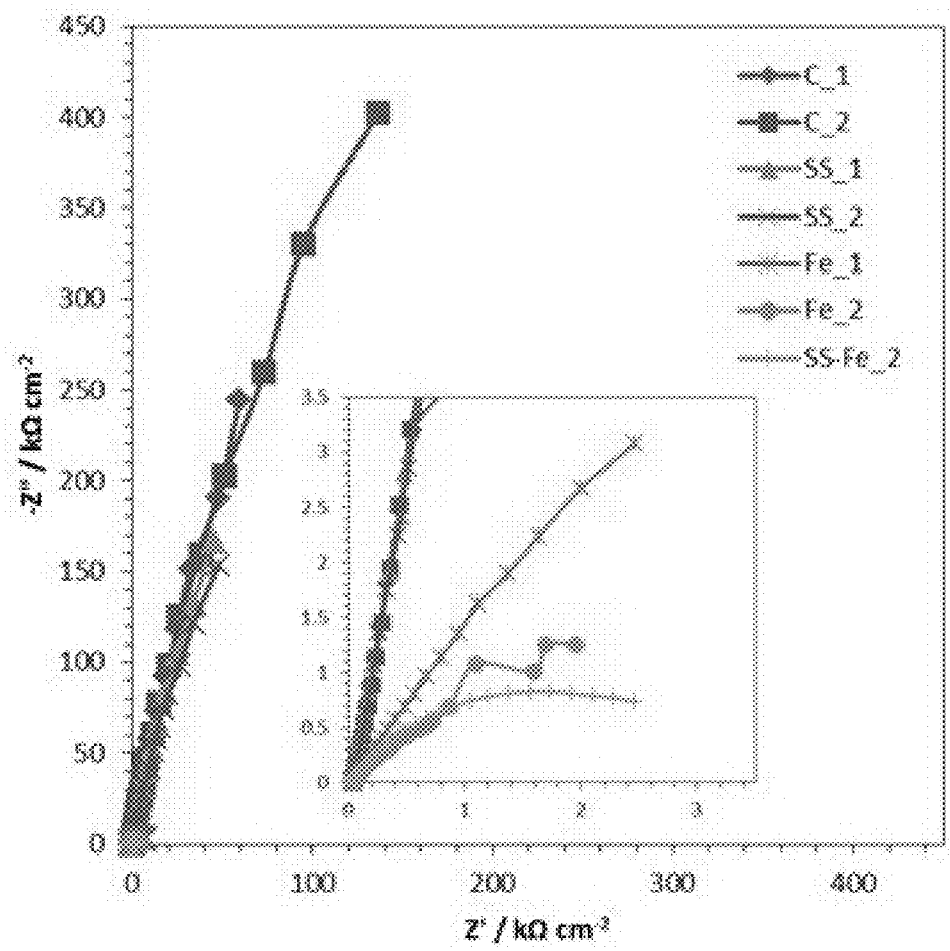
FIG. 5, in an X-Y graph, illustrates electrical impedance spectroscopy (EIS) measurements for various vapor deposited films using the setup of FIG. 2, (C: control; SS; stainless steel; Fe: iron; SS-Fe: mix of SS and Fe). Z' and Z" are the real and imaginary components of the impedance in a Nyquist plot. Control (C_1, C_2) and SS showed a similar behaviour. Fe and SS-Fe showed a similar behavior, with a more negative corrosion potential and an apparent higher corrosion rate with respect to SS and the control samples. On the left side (High frequency side) a semicircle indicates capacitive behavior.
Figure 6:
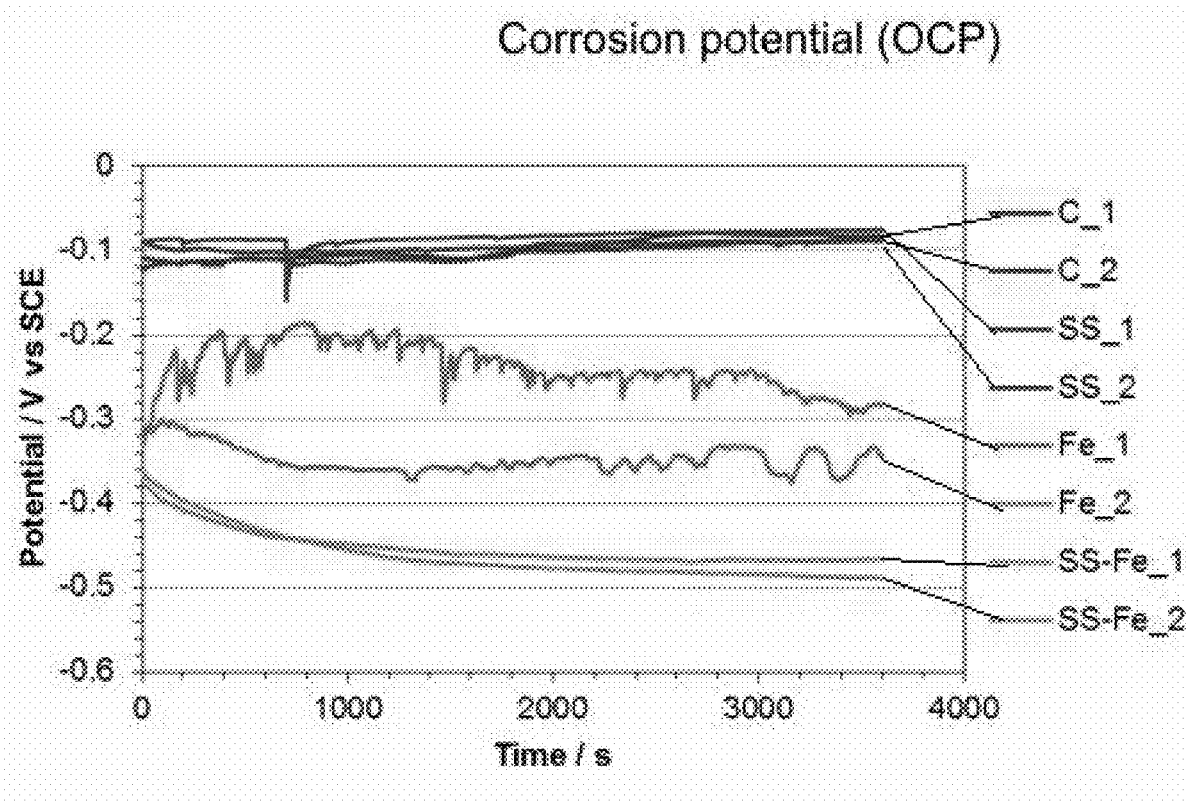
FIG. 6, in an X-Y graph, illustrates the open circuit potential (OCP) of various vapor deposited films using the setup of FIG. 2 relative to a saturated calomel electrode (SCE), (C: control; SS: stainless steel; Fe: iron; SS-Fe: mix of SS and Fe); lower (more negative) values indicate more corrosion susceptibility.
Figure 7:
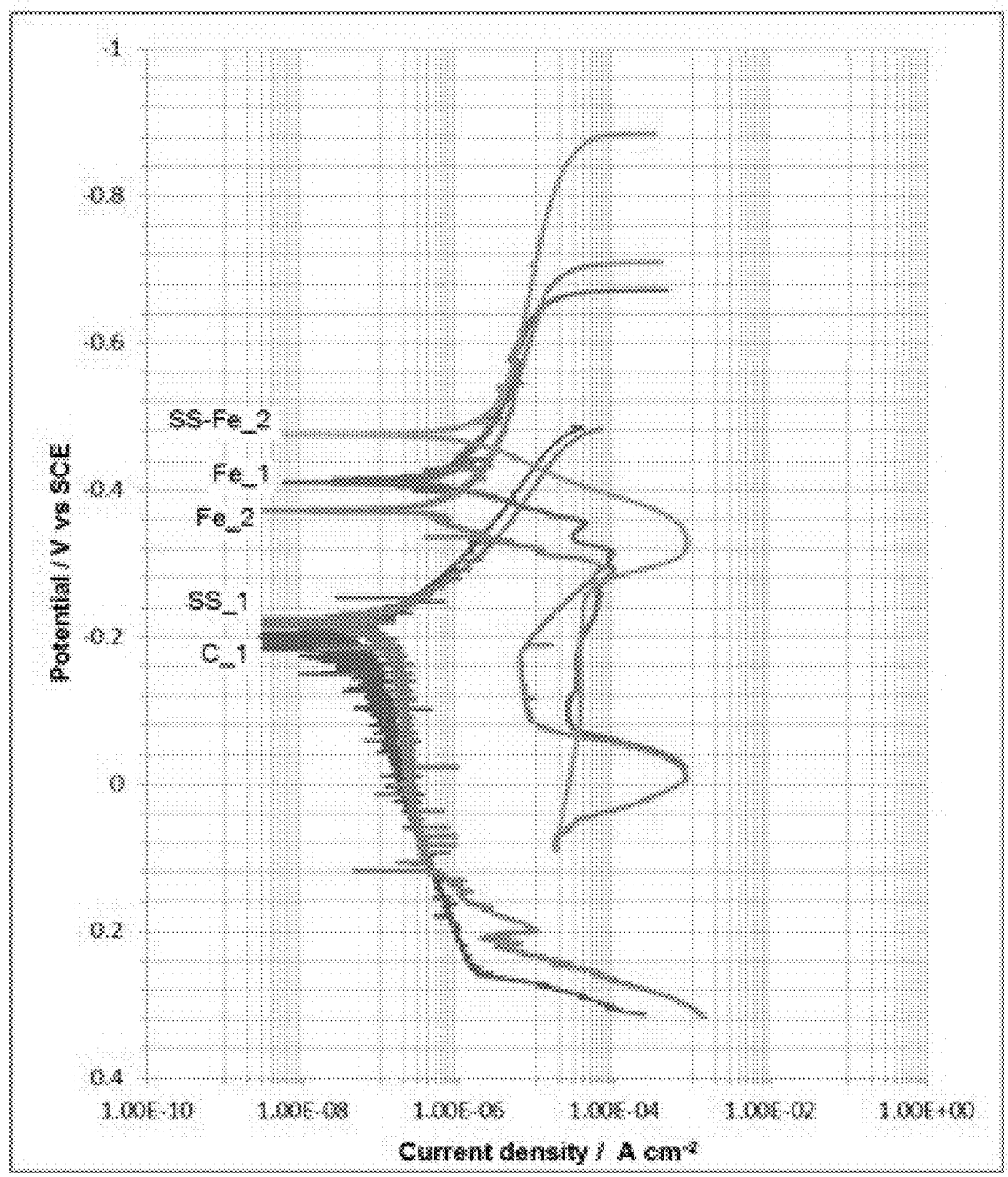
FIG. 7, in an X-Y graph, illustrates the potentiodynamic polarization of various vapor deposited films using the setup of FIG. 2 relative to a saturated calomel electrode (SCE), (C: control; SS; stainless steel; Fe: iron; SS-Fe: mix of SS and Fe)

The results of the electrochemical techniques are shown in FIGS. 5 to 7. OCP results (FIG. 6) show a more negative corrosion potential and thus higher corrosion susceptibility for the Fe-SS samples. The higher corrosion susceptibility of Fe-SS samples was confirmed by PP (FIG. 7) and EIS (FIG. 5) measurements, showing a decreasing corrosion resistance in the order SS>Fe>Fe-SS.

Figure 8:
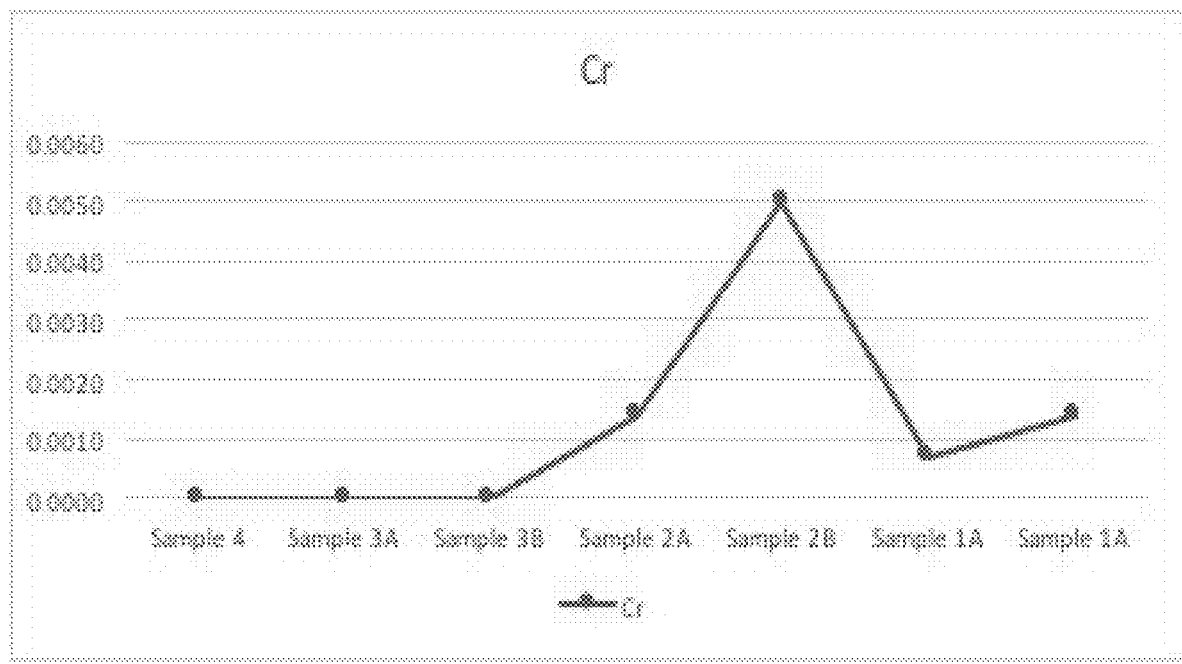
FIG. 8, in an X-Y graph, illustrates chromium release in saline solution as a function of time measured through Inductive Coupled Plasma (ICP) technique for a mixed SS-Fe film deposited using the setup of FIG. 2. Sample 1A=9 days, 2A=3 days, 3A=1 day, 4=blank solution (B=duplicate)

ICP results are shown in FIG. 8. The starting solution contained NaCl with Mg and K as a contaminant. The ceramic under the Stainless steel also contained K, Ca, Si all above 1% which is the limit of detection of the XPS. Hence, any Ca, K, Si, and Na should be excluded from the interpretation because it may have originated from the ceramic substrate.

Figure 9:
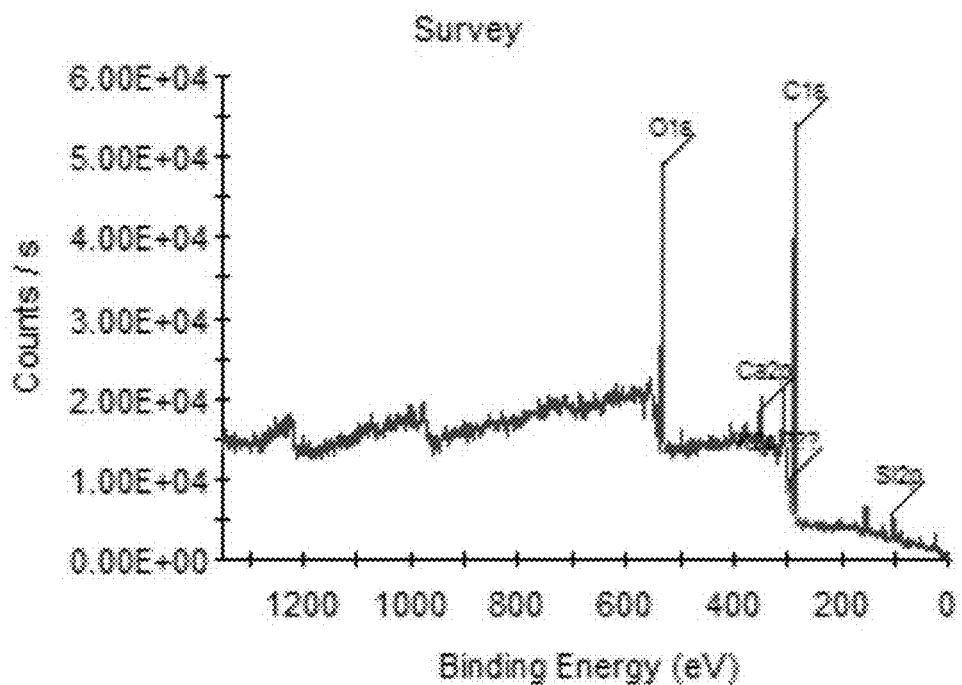
FIG. 9, in an X-Y graph, illustrate X-ray photoelectron spectroscopy (XPS) results showing the chemical composition of a bare ceramic substrate prior to coating in the setup of FIG. 2.
Figure 10:
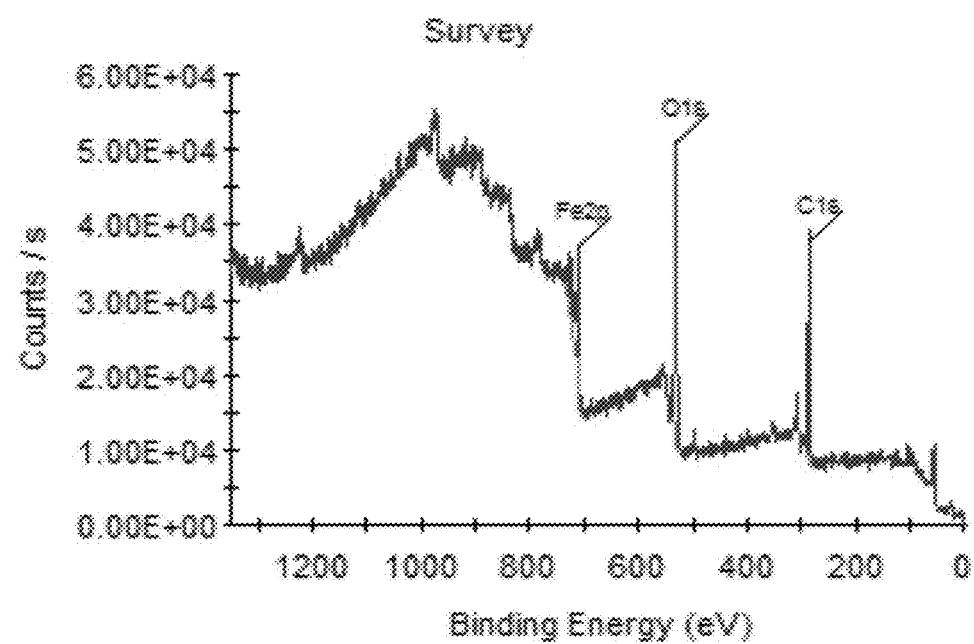
FIG. 10, in an X-Y graph, illustrate X-ray photoelectron spectroscopy (XPS) results showing the chemical composition of the ceramic substrate after coating with a 1:1 mixture of SS and Fe using the setup of FIG. 2.

FIGS. 9 and 10 illustrate results of XPS measurements of 1) bare ceramic (FIG. 9) and 2) Fe-SS ratio 1:1 on ceramic (FIG. 10). In FIG. 9, the detected elements correspond to the ceramic composition: K and Ca. Si and C are usually external contaminants from ambience and manipulation. On FIG. 10, the detected elements are Fe mainly, oxygen and carbon.

PVD coating tests were performed on ceramic and metallic substrates with different ratios of Fe-SS (1:1 and 4:1). SEM and TEM microscope micrographs showed the presence of a homogeneous and uniform structure of intermixed particulate material of SS and Fe with the presence of nano and micron sized particles. From immersion tests, the ratio of Fe to SS 4:1 seemed to provide a faster degradation. That meaning that a tuned ratio of Fe and SS can form a galvanic couple and result in biodegradable stents with corrosion tuning possibilities Electrochemical tests showed faster degradation rates on coatings where Fe and SS are combined, compared to Fe, SS and plasma-deposited SS coatings. A tuned ratio of Fe and SS can form a galvanic couple following for an 'optimal' degradation rate and thus result in bioresorbable stents with tailored dissolution rates.

ICP analysis from 9 days of immersion in saline solution show the presence of the elements coming from the SS. Concerning the Cr content, the higher amount observed was after 3 days of immersion: 0.0050 ppm compared to Fe showing 0.0196 ppm during the same observation. XPS analysis on coated ceramics with Fe-SS ratio 1:1 showed the presence of Fe mainly. This means that the amount of the rest of SS chemical elements are lower than 1%.

Although the present invention has been described hereinabove by way of preferred embodiments thereof, it can be modified, without departing from the spirit and nature of the subject invention as defined in the appended claims.

What is claimed is:

1. A method for manufacturing a bioresorbable stent that is entirely made of bioresorbable material, the method comprising the steps of:
   (a) providing in a vapor deposition chamber a substrate including a substrate material, an anodic source made of an anodic material, and a cathodic source made of a cathodic material, wherein the anodic material and cathodic material are respectively iron and stainless steel, and wherein the vapor deposition chamber is a cathodic arc physical vapor deposition chamber;
   (b) operating the vapor deposition chamber to vaporize simultaneously the anodic and cathodic materials from the anodic and cathodic sources and depositing the vaporized cathodic and anodic materials on the substrate to produce a coated substrate including the substrate material coated by a bioresorbable coating formed by deposition of the vaporized cathodic and anodic materials, the bioresorbable coating having grains of different compositions bound to each other; and
   (c) obtaining the bioresorbable stent consisting of the bioresorbable coating;
   wherein the anodic and cathodic materials are deposited in a predetermined ratio and are selected so that bioresorption of the whole bioresorbable stent is promoted by galvanic corrosion between the grains when the bioresorbable stent is implanted in vivo; wherein the bioresorbable coating is in the form of a continuous material including the grains, the grains being smaller than 100 nm.

2. The method as defined in claim 1, wherein the substrate material differs from both the anodic and cathodic materials.

3. The method as defined in claim 1, wherein the substrate material is identical to one of the anodic and cathodic materials.

4. The method as defined in claim 1, wherein the predetermined ratio is from about 1:1 to about 4:1 weight for weight (w/w) in the anodic material with respect to the cathodic material.

5. The method as defined in claim 1, wherein the substrate material differs from the anodic and cathodic materials, and step (c) includes
   exposing at least part of the substrate material; and
   removing at least part of the substrate material from the coated substrate.

6. The method as defined in claim 5, wherein removing at least part of the substrate material includes removing essentially all the substrate material so that the bioresorbable stent is made essentially of the deposited bioresorbable coating.

7. The method as defined in claim 6, wherein the substrate material is soluble in a solvent, removing essentially all the substrate material including dissolving the substrate material in the solvent.

8. The method as defined in claim 6, wherein step (c) further includes cutting out portions of the bioresorbable coating.

9. The method as defined in claim 6, wherein the substrate is substantially cylindrical and defines two substantially opposed cylinder end surfaces, the method further comprising covering with a covering element at least one of the cylinder end surfaces before step (b) and wherein step (c) includes removing the covering element.

10. The method as defined in claim 1, wherein the substrate provided in step (a) includes a plurality of struts, the substrate provided in step (a) being entirely covered with the anodic and cathodic materials after completion of step (b).

11. The method as defined in claim 1, wherein at least 99% of the grains are smaller than 100 nm.

12. The method as defined in claim 11, wherein at least 99% of the grains are smaller than 10 nm.

13. The method as defined in claim 1, wherein particles larger than 100 nm are dispersed in the continuous material.

14. The method as defined in claim 1, wherein the substrate is biased at a negative voltage.

15. The method as defined in claim 14, wherein the negative voltage is between −10V and −1000V.

16. The method as defined in claim 15, wherein the negative voltage is about −150V.

17. The method as defined in claim 1, wherein step (b) includes rotating the substrate while operating the vapor deposition chamber.

18. The method as defined in claim 1, wherein the substrate includes a metal coated with a carbon nanotube forest including carbon nanotubes, the carbon nanotubes being exposed to the vaporized cathodic and anodic materials in step (b).

* * * * *